United States Patent
Qin et al.

(10) Patent No.: US 9,161,542 B2
(45) Date of Patent: Oct. 20, 2015

(54) PESTICIDAL COMPOSITIONS AND RELATED METHODS

(75) Inventors: Kuide Qin, Westfield, IN (US); Melissa Hays, Freeland, MI (US); Dennis G. Wujek, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 18 days.

(21) Appl. No.: 13/480,901

(22) Filed: May 25, 2012

(65) Prior Publication Data

US 2012/0302611 A1    Nov. 29, 2012

Related U.S. Application Data

(60) Provisional application No. 61/490,479, filed on May 26, 2011.

(51) Int. Cl.
*A01N 25/00* (2006.01)
*A01N 47/40* (2006.01)

(52) U.S. Cl.
CPC .............. *A01N 47/40* (2013.01); *A01N 25/006* (2013.01)

(58) Field of Classification Search
CPC .................................................... A01N 25/006
See application file for complete search history.

(56) References Cited

U.S. PATENT DOCUMENTS

| | | | |
|---|---|---|---|
| 6,835,719 B2 * | 12/2004 | Parker et al. ..................... 514/65 |
| 8,598,084 B2 * | 12/2013 | Satchivi et al. ............... 504/118 |
| 2001/0027217 A1 * | 10/2001 | Jaetsch et al. .................. 514/731 |
| 2010/0113543 A1 | 5/2010 | Israels et al. |
| 2011/0046194 A1 | 2/2011 | Alig et al. |
| 2011/0052555 A1 | 3/2011 | Coqueron et al. |
| 2011/0118122 A1 | 5/2011 | Niyaz et al. |
| 2011/0207606 A1 * | 8/2011 | Satchivi et al. ............... 504/105 |

FOREIGN PATENT DOCUMENTS

| WO | WO2006/060029 | 6/2006 |
|---|---|---|
| WO | 2007095229 A2 | 8/2007 |
| WO | WO2007/149134 | 12/2007 |
| WO | 2010040623 A1 | 4/2010 |
| WO | WO-2010/040623 A1 * | 4/2010 |
| WO | WO2010/118833 | 10/2010 |

OTHER PUBLICATIONS

International Search Report and Written Opinion for International Application No. PCT/US2012/039543, dated Dec. 27, 2012.

* cited by examiner

*Primary Examiner* — Ali Soroush
(74) *Attorney, Agent, or Firm* — Carl D. Corvin; TraskBritt, P.C.

(57) ABSTRACT

Pesticidal compositions that improve soil residual efficacy of sulfoxaflor are disclosed.

9 Claims, No Drawings

PESTICIDAL COMPOSITIONS AND RELATED METHODS

CROSS-REFERENCE TO RELATED APPLICATION

This application claims the benefit of U.S. Provisional Patent Application Ser. No. 61/490,479, filed May 26, 2011, the disclosure of which is hereby incorporated herein in its entirety by this reference.

TECHNICAL FIELD

Various aspects and embodiments relate generally to formulations of pesticidal compositions that exhibit advantageous biological, commercial and/or environmental properties.

BACKGROUND

Controlling insect population is essential to modern agriculture, food storage, and hygiene. Currently, safe and effective encapsulated insecticidal formulations play a significant role in controlling insect populations. Properties of useful encapsulated insecticidal formulations include good efficacy against targeted pests, including good initial toxicity against targeted insects, ease of handling, stability, advantageous residence times in the environment and, in some instances, a long effective period of insecticidal activity after its application to an area.

Unfortunately, most insecticide formulations, especially liquid based preparations, lose their efficacy relatively soon after application. Such insecticide formulations must, therefore, be reapplied to ensure insect control. Additionally, formulations with a short period of post application activity may result in periods of time during which an area is vulnerable to infestation by pests. This creates a need to periodically apply various insecticidal formulations in order to control continuing pest infestations or to prevent their occurrence, and to increase the amount of insecticides that must be used, which results in increased cost associated with their shipping, handling and application.

BRIEF SUMMARY

Embodiments of the present disclosure include pesticidal compositions. Such pesticidal compositions may include a base formulation comprising a weight ratio of sulfoxaflor to a carrier of between about 1-to-5 and about 1-to-1 and a co-formulant comprising at least one of a surfactant, a dispersant, a thickener, a pH buffer, an antifreezing agent, and a diluent. The carrier may include at least one of a phenol, a cyclodextrin, an aniline, and a pyridine.

In further embodiments the pesticidal compositions may include a weight ratio of sulfoxaflor to a carrier (i.e., a phenol, a cyclodextrin, an aniline, and/or a pyridine) of between about 1-to-5 and about 1-to-1 and a co-formulant that includes at least one of a liquid diluent and a self-emulsifiable ester.

Embodiments of the present disclosure further include methods of forming a pesticidal composition. Such methods may include dissolving sulfoxaflor and a carrier comprising a phenol, a cyclodextrin, an aniline, and/or a pyridine in at least one solvent to form a solution and removing the at least one solvent from the solution by drying to form a base formulation.

In additional embodiments, such methods may include forming a mixture of at least one of a phenol, a cyclodextrin, an aniline, and a pyridine and sulfoxaflor in a polar solvent, stirring the mixture, drying the mixture to form a base formulation, and combining the base formulation with at least one co-formulant to form the pesticidal composition.

In yet further embodiments, methods of controlling pests include applying a pesticidal composition of the present disclosure near a population of insects.

Embodiments of the present disclosure further include methods of extending the effective field life of an insecticide. Such methods may include dissolving sulfoxaflor and at least one of a phenol, a cyclodextrin, an aniline, and a pyridine in at least one solvent to form a base formulation and combining the base formulation with at least one co-formulant.

DETAILED DESCRIPTION

Embodiments of pesticidal compositions that improve soil residual efficacy of sulfoxaflor are disclosed. The compositions may be formed by combining sulfoxaflor with a carrier, such as a phenol compound, a cyclodextrin compound, an aniline compound, and/or a pyridine compound, to form a base formulation which may be combined with other ingredients to form the composition. In the pesticidal compositions, the sulfoxaflor retains its insecticidal efficacy. For example, the pesticidal composition may effectively kill or repel insects for at least 14 days after their application. Such improved stability may be obtained by preparing a base formulation that includes a weight ratio of about 2:1 of a carrier:sulfoxaflor, and combining the base formulation with at least one co-formulant. Methods of forming the pesticidal compositions are also disclosed.

As used herein, the term "pest" means and includes invertebrates, organisms and microorganisms (including pathogens) that negatively affect plants or animals. This includes organisms that spread disease and/or damage the host and/or compete for host nutrients. In addition, plant pests are organisms known to associate with plants and which, as a result of that association, cause a detrimental effect on the plant's health and vigor. Plant pests include but are not limited to fungi, bacteria, insects, arachnids, nematodes, slugs, snails, etc.

In a particular embodiment, the composition may be used to control pests in the Phyla Nematoda and/or Arthropoda. In another embodiment, the composition may be used to control pests in the Subphyla Chelicerata, Myriapoda, and/or Hexapoda. In yet another embodiment, the composition may be used to control pests in the Classes of Arachnida, Symphyla, and/or Insecta. In an alternate embodiment, the composition may be used to control pests of the Order Homoptera.

In another embodiment, the composition may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus,* and *Pthirus pubis.*

In yet another embodiment, the composition may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Panto-* morus spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In an alternative embodiment, the composition may be used to control pests of the Order Dermaptera.

In another embodiment, the composition may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In yet another embodiment, the composition may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In a particular embodiment, the composition may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, kerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

In another embodiment, the composition may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni*, and *Tapinoma sessile*.

In an alternative embodiment, the composition may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the composition may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabu-*

*lifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Theela basilides, Tineola bisselliella, Trichoplusia ni, Tuta absoluta, Zeuzera coffeae,* and *Zeuzera pyrina.*

In a particular embodiment, the composition may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the composition may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In yet another embodiment, the composition may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

In an alternative embodiment, the composition may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the composition may be used to control pests of the Order Thysanura. A non-exhaustive list of particular genera includes, but is not limited to, *Lepisma* spp. and *Thermobia* spp.

In yet another embodiment, the composition may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In a particular embodiment, the composition may be used to control pest of the Order Symphyla. A non-exhaustive list of particular sp. includes, but is not limited to, *Scutigerella immaculata.*

In another embodiment, the composition may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

The term "pesticide," as used herein, means and includes any substance that may be used to control agricultural, natural, environmental, and domestic/household pests, such as insects, fungi, bacteria, and viruses.

The terms "control" and "controlling," as used herein, mean and include killing, eradication, arresting in growth, inhibition, reducing in number and/or imparting sterility.

The term "insecticide," as used herein, refers to a specific category of pesticides used for controlling insects.

As used herein, the term "sulfoxaflor" is the provisionally approved name for [methyl(oxo){1-[6-(trifluoromethyl)-3-pyridyl]ethyl}-$\lambda^6$-sulfanylidene]cyanamide (IUPAC designation) which is also known as N-[methyloxido[1-[6-(trifluoromethyl)-3-pyridinyl]ethyl]-$\lambda^4$-sulfanylidene]cyanamide (CAS Name, CAS registry number 946578-00-3). Sulfoxaflor is a mixture of four possible stereoisomers, the chemical structures of which are as follows:

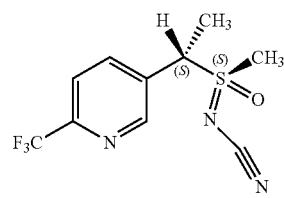

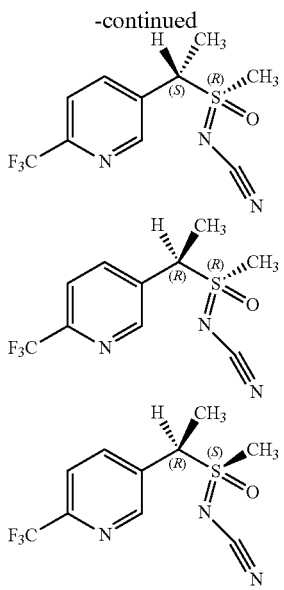

As used herein, the term "wt %" refers to a percent of a particular component by weight in a composition based on an overall weight of a composition.

Sulfoxaflor demonstrates efficacy against a broad spectrum of insects. Sulfoxaflor has demonstrated excellent acute efficacy against a broad spectrum of sap-feeding insects like aphids. Sulfoxaflor has also been shown to have a high level of efficacy against hard to control true bugs, such as Lygus. Additionally, sulfoxaflor possesses high levels of intrinsic activity and controls insect populations resistant to neonicotinoid and other insecticide modes of action including the organophosphates, pyrethroids, and carbamates. For example, foliar application of sulfoxaflor has demonstrated efficacy under field conditions that is equal or superior to neonicotinoid compounds at equivalent or lower use rates, particularly for aphid control.

However, the residual activity of sulfoxaflor in soil applications is relatively less than desired. In microbially active soils, the half-life of sulfoxaflor may be shorter than desired. The relatively less than desired residual activity in soil may be caused by degradation of sulfoxaflor by microbial metabolism. Regardless of the specific mechanism of action involved, protection is desired in order increase its lifetime in soil and slow the rate of loss due to degradation.

The pesticidal compositions may include a unique combination of co-formulants that, when combined, increase the soil half-life of sulfoxaflor while maintaining pesticidal properties. The pesticidal composition may be formed by dissolving the sulfoxaflor and the carrier in at least one solvent to form a base formulation, and combining the base formulation with one or more co-formulants. Before adding the co-formulants, the base formulation may be dried to remove the solvent using a process like conventional vacuum drying. Suitable co-formulants include, but are not limited to, at least one of a surfactant, a dispersant, a thickener, a pH buffer, an antifreezing agent, and a diluent.

For example, sulfoxaflor and a carrier (e.g., a phenol, a cyclodextrin, an aniline, and/or a pyridine) may be dissolved in a solvent to form a base formulation that includes a weight ratio of sulfoxaflor:carrier of between about 1:5 and about 1:1 and, more particularly, between about 1:4 and about 1:1 and, still more particularly, between about 1:3 and about 1:1.

Sulfoxaflor may be synthesized using methods such as those described in International Patent Publication No. WO2007/095229.

Examples of suitable phenols that may be used as carriers include, but are not limited to, 4-tert-butylphenol, 2,4-di-tert-butylphenol, 4-methylphenol, 4-phenylphenol, 2-phenylphenol, 4-chlorophenol, 4-(1,1-dimethylpropyl)-phenol, 4-(1,1,2,2-tetramethylpropyl)-phenol, 4-dodecylphenol, 4-cyclohexylphenol, 4-(perchlorocyclohexyl)-phenol, 4-(4-methoxycyclohexyl)-phenol, 4-benzylphenol, 4-(1-methyl-1-phenylethyl)-phenol, 4-[1-methyl-1-(4-chlorophenyl)-ethyl]-phenol, 4-(2-chlorophenyl)-phenol, 4-(4-fluorophenyl)-phenol, 4-(4-tert-butylphenyl)-phenol, 4-(pentachlorophenyl)-phenol, 4-(4-nitrophenyl)-phenol, 4-(pentachlorophenyl)-phenol, 4-(2-pyridyl)-phenol, 4-(2-oxazolyl)-phenol, 4-(4-pyridyl)-phenol, 4-(4-morpholinyl)-phenol, 2-chloro-4-methylphenol, 3-chloro-4-tert-butyl-phenol, 2-fluoro 4-tert-butylphenol, 2-methoxy-4-tert-butylphenol, 2-phenoxy-4-tert-butylphenol, 3-(4-tert-butylphenoxy)-4-tert-butylphenol, 3-(4-fluorophenoxy)-4-tert-butylphenol, 4-methoxyphenol, 4-phenoxyphenol, 4-hydroxydiphenyl-sulphone, 4-hydroxydiphenylcarbonate, 4-fluorophenol, 2,4-difluorophenol, 2,4-dichlorophenol, 3,4-dichlorophenol, 4-bromophenol, 4-iodophenol, 4-(N-methyl-amino)-phenol, 4-(N-phenylamino)-phenol, 4-N-methyl-N-phenylaminophenol, 4-hydroxybenzophenone, 4-benzoic acid-4-hydroxyphenyl ester, N-benzoyl-4-aminophenol, N-(4-hydroxyphenyl)-ethylurethane, 3,4,5-trichlorophenol, 2,3,4-trichlorophenol, 2,3-dichloro-4-methylphenol, and 4-chloro-3,5-dimethylphenol.

Examples of suitable cyclodextrin that may be used as carriers include, but are not limited to, β-cyclodextrin, α-cyclodextrin and γ-cyclodextrin.

An example of an aniline that may be used as a carrier includes, but is not limited to, 2,4,6-tri-tert-butylaniline.

An example of a pyridine that may be used as a carrier includes, but is not limited to, 4-aminopyridine.

Examples of suitable solvents include, but are not limited to, acetone, xylene and other ketones, alcohols, esters, aromatic hydrocarbons, aliphatic hydrocarbons, ethers and water, and mixtures thereof.

One or more carriers and sulfoxaflor may be added to a polar solvent (e.g., acetone, methanol, ethanol, water, etc.) and may be dissolved therein by stirring at about room temperature (i.e., from about 20° C. to about 25° C.) to form a mixture. The sulfoxaflor:carrier weight ratio of the mixture may be between about 1:5 and about 1:1 and, more particularly, between about 1:3 and about 1:1. In embodiments in which the pesticidal composition includes a phenol as a carrier, the pesticidal composition may include a weight ratio of sulfoxaflor:phenol of between about 1:2 and about 1:1. In embodiments in which the pesticidal composition includes a cyclodextrin as a carrier, the pesticidal composition may include a weight ratio of sulfoxaflor:cyclodextrin of between about 1:6 and about 1:4. In some embodiments, the carrier (i.e., a cyclodextrin, a phenol, an aniline, and/or a pyridine) may be dissolved individually to form a carrier solution and a sulfoxaflor solution and the solutions may be combined to form the mixture. For example, in embodiments in which the carrier comprises a cyclodextrin, the cyclodextrin may be dissolved in a polar solvent (e.g., water) to form the cyclodextrin solution and the sulfoxaflor may be dissolved in an alcohol (e.g., methanol, ethanol, etc.) to form the sulfoxaflor solution, and the cyclodextrin solution may be combined with the sulfoxaflor solution to form the mixture. The mixture may then be dried to form a base formulation. For example, the mixture may be dried by placing the mixture in a vacuum oven at about room temperature until the solvent has at least partially evaporated.

The base formulation comprising sulfoxaflor and carrier(s) may be combined with at least one of the co-formulants to form the composition. In some embodiments, the base formulation may be combined with at least one of a surfactant, a dispersant, a thickener, a pH buffer, an antifreezing agent, and a diluent.

The pesticidal composition may include, for example, between about 0.1 wt % and about 15 wt % and, more particularly, between about 0.5 wt % and about 10 and, more particularly, between about 1 wt % and about 5 wt % of at least one surfactant. Suitable surfactants include, but are not limited to, polymeric surfactants, sulfates of alkoxylated alkanoles, fatty alcohol polyglycol ethers, and polysorbates. By way of example and not limitation, the surfactant may be a C12-alcohol ethoxylate, such as ethoxylated lauryl alcohol surfactant. A polymeric surfactant, such as that commercially available from Huntsman International LLC (The Woodlands, Tex.) under the trademark TERSPERSE® 2500 series, may also be employed. An alcohol polyglycol ether, such as ETHYLAN™ NS 500 LQ alcohol polyglycol ether, which is commercially available from Akzo Nobel (Chicago, Ill.), may also be employed. By way of example and not limitation, the pesticidal composition may include between about 0.05 wt % and about 2 wt % and, more particularly, about 0.3 wt % of the AGNIQUE® DMF 1125, between about 0.5 wt % and about 4 wt % and, more particularly, about 1.9 wt % of the TERSPERSE® 2500 series and between about 0.5 wt % and about 4 wt % and, more particularly, about 1.9 wt % of the ETHYLAN™ NS 500 LQ.

The pesticidal composition may include, for example, between about 0.1 wt % and about 5 wt % and, more particularly, between about 0.1 wt % and about 2 wt % and, more particularly, between about 0.1 wt % and about 1.5 wt % of at least one thickener. By way of example and not limitation, the thickener may include a microcrystalline cellulose gel, such as AVICEL® CL 611 thickener, which is commercially available from FMC Corporation (Philadelphia, Pa.), and/or an organic gum (e.g., xanthan gum such as that commercially available from CP Kelco U.S., Inc. (Atlanta, Ga.) under the trademark KELZAN® S xanthan gum). For example, the composition may include about 1.1 wt % of the AVICEL® CL 611 thickener and about 0.2 wt % of the KELZAN® S xanthan gum.

The pesticidal composition may include, for example, between about 1 wt % and about 10 wt % and, more particularly, between about 1 wt % and about 5 wt % and, more particularly, between about 1 wt % and about 3 wt % of at least one dispersant. By way of example and not limitation, the dispersant may include MORWET® D-360 powder, which includes a blend of an alkyl naphthalene sulfonate condensate and lignosulfonate and which is commercially available from Akzo Nobel. For example, the pesticidal composition may include about 2.9 wt % of the MORWET® D-360 powder.

The pesticidal composition may optionally include, for example, between about 0.01 wt % and about 2 wt % and, more particularly, between about 0.01 wt % and about 1 wt % and, more particularly, between about 0.05 wt % and about 0.5 wt % of at least one preservative. By way of non-limiting example, the preservative may be an aqueous solution of 1,2-benzisothiazolin-3-one, such as PROXEL® GXL preservative, which is commercially available from Arch UK Biocides Limited (England). For example, the composition may include about 0.1 wt % of the PROXEL® GXL preservative.

The pesticidal composition may include, for example, between about 0.01 wt % and about 5 wt % and, more particularly, between about 0.01 wt % and about 2 wt % and, more particularly, between about 0.1 wt % and about 1 wt % of at least one pH buffer. The buffer may include, for example, an aqueous solution of a weak acid and its conjugate base, or a weak base and its conjugate acid such as, for example, citric acid, ascorbic acid, potassium phosphate or sodium phosphate. The buffer solution may be formulated to maintain a desired pH of 2-6, particularly a pH of 2-4 of the pesticidal composition. For example, the pesticidal composition may include about 0.2 wt % of citric acid as a buffer.

The pesticidal composition may include, for example, between about 0.1 wt % and about 10 wt % and, more particularly, between about 1 wt % and about 10 wt % and, more particularly, between about 1 wt % and about 5 wt % of at least one antifreezing agent. Suitable antifreezing agents include, but are not limited to, propylene glycol, ethylene glycol and glycerol, and mixtures thereof. For example, the propylene glycol may comprise between about 2 wt % and about 10 wt % and, more particularly, about 4 wt % and about 6 wt % of the pesticidal composition.

In another embodiment, the base formulation may be combined with a non-aqueous liquid diluent and a self-emulsifiable ester. Examples of suitable non-aqueous liquid diluent include, but are not limited to, liquid diluent including benzene, alcohols, acetone, xylene, methylnaphthalene, dioxane and cyclohexanone. Examples of self-emulsifiable esters include, but are not limited to, succinate triglyceride oil derived from maleating triglyceride oil such as VEG-ESTER® additives, which are commercially available from Lubrizol, Inc. For example, the pesticidal composition may be formed by combining between about 10 wt % and about 30 wt % of the base formulation with between about 30 wt % and about 50 wt % of each of cyclohexanone and VEG-ESTER® GY-350 additive.

The pesticidal composition may be applied directly to, or to a surface adjacent to, a population of insects. The pesticidal composition may generally be used in amounts that bring from about 0.1 grams per hectare to about 5000 grams per hectare of sulfoxaflor to an area to provide control. In particular embodiments, amounts from about 1 grams per hectare to about 500 grams per hectare are generally preferred, and amounts from about 12 gram per hectare to about 150-grams per hectare are generally more preferred.

The area to which the pesticidal composition is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use the pesticidal composition include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted.

Controlling pests generally means that pest populations, pest activity, or both, are reduced in an area. This can come about when: pest populations are repulsed from an area; when pests are incapacitated in or around an area; pests are sterilized in an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The pesticidal composition may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). The pesticidal composition may be applied to the foliar and fruiting portions of plants to control pests. The pesticidal composition will either come in direct contact with the pest, or the pest will consume the pesticide when eating leaf, fruit mass, or extracting sap, that contains the pesticide. The pesticidal composition can also be applied to the soil, and when applied in this manner, root and stem feeding pests can be controlled. The roots can absorb a molecule taking it up into the foliar portions of the plant to control above ground chewing and sap feeding pests.

Systemic movement of pesticides in plants may be utilized to control pests on one portion of the plant by applying (for example by spraying an area) the pesticidal composition to a different portion of the plant. For example, control of foliar-feeding insects can be achieved by drip irrigation or furrow application, by treating the soil with for example pre- or post-planting soil drench, or by treating the seeds of a plant before planting with the pesticidal composition.

The following examples serve to explain embodiments of the present disclosure in more detail. These examples are not to be construed as being exhaustive or exclusive as to the scope of this disclosure.

EXAMPLES

Example 1

Preparation of Insecticidal Formulations Including Phenols

In a clean vessel, about 2 g of the phenol listed in Table 1 and about 1 g of sulfoxaflor technical grade was added to about 10 g of acetone solvent under constant mixing at room temperature. After both the phenol and the sulfoxaflor were completely dissolved, the homogenous mixture was gently stirred for at least 3 hours. The mixture was then dried in a vacuum oven at about 24° C. and about 304.8 mmHg (about 12 inches Hg) for about 30 minutes. The sample was collected for further formulations. The procedure was repeated for each carrier compound for A to E respectively. The composition of each of the resulting mixtures, known herein as the base formulations, is shown in Table 1.

TABLE 1

Base Formulations Prepared from A Phenol and Sulfoxaflor

| Base Formulation | Phenol | Phenol: Sulfoxaflor (wt basis) | Melting Point of Base Formulation |
|---|---|---|---|
| A | 2,4-di-tert-butylphenol m.p. = 52-57° C. | 2:1 | 158° C. |
| B | 4-phenylphenol m.p. = 163.5-165.4° C. | 2:1 | 96.8° C. |
| C | 4-tert-butylphenol m.p. = 98.7° C. | 2:1 | 82.4° C. |
| D | 4-chlorophenol m.p. = 41-45° C. | 2:1 | 131.3° C. |
| E | 2-phenylphenol m.p. = 56° C. | 2:1 | 139.3° C. |

Melting points were determined for each of the base formulations using differential scanning calorimetry (DSC). Table 1 provides melting points (m.p.) for each of the phenols and the melting points of each of the base formulations made from those phenols. Sulfoxaflor has a melting point of between about 107.8° C. and about 109.8° C. The base formulations A, D and E each have a substantially increased melting point than the constituents (i.e., the phenol and the sulfoxaflor) from which they are made. The base formulations B and C each have a substantially reduced melting point than the constituents (i.e., the phenol and the sulfoxaflor) from which they are made. While not wishing to be bound by any particular theory, it is believed that the difference in melting points may indicate an inter-molecular interaction, an intra-molecular interaction, or complexation between the phenol and the sulfoxaflor.

In order to apply the base formulations (A, B, C, D and E) obtained as described in the procedure above in spray applications to control insects, the base formulations were combined with co-formulants as shown in Tables 2 and 3 to form pesticidal compositions. A pesticidal composition was formed from each of base formulations B and C using the ingredients listed in Table 2. To prepare the pesticidal compositions from base formulations B and C, water was added to a clean vessel and the remaining ingredients shown in Table 2 were then added in no particular order. The pesticidal compositions were finished by mixing all ingredients to homogeneity.

TABLE 2

Compositions including B and C

| Ingredient | wt % |
|---|---|
| Base formulation B or C | 9.5 |
| AGNIQUE ® DFM 112S | 0.3 |
| AVICEL ® CL 611 | 1.1 |
| TERSPERSE | 1.9 |
| MORWET ® D-360 | 2.9 |
| ETHYLAN ™ NS 500 LQ | 1.9 |
| Propylene Glycol | 3.8 |
| PROXEL ® GXL | 0.1 |
| KELZAN ® xanthan gum | 0.2 |
| Citric acid | 0.2 |
| Water | 78.1 |

Pesticidal compositions were also formed from each of base formulations A, D and E using the ingredients listed in Table 3. To form the pesticidal compositions, cyclohexanone was first added to a clean vessel, then one of base formulations A, D or E was added to the vessel under constant mixing. The VEG-ESTER® 350 was finally added to the vessel to finish the pesticidal composition.

TABLE 3

Compositions including Base Formulations A, D and E

| Base Formulation A, D or E | 18.7 |
|---|---|
| Cyclohexanone | 40.7 |
| VEG-ESTER ® GY-350 | 40.6 |

The pesticidal compositions formed from base formulations A, B, C, D and E are respectively referred to herein as compositions A, B, C, D and E. Each of these compositions includes sulfoxaflor and may be readily diluted in water to form a solution or mixture. Such a solution or mixture may be applied, for example, using a conventional agricultural pressure node atomization process also known as spray application.

Example 2

Insecticidal Efficacy of Compositions A, B, C, D and E

Soil known to have active microbes was placed in one ounce cups. Each of the compositions formed from base formulations A, B, C, D and E (as described in Example 1) were diluted in water such that a concentration of the sulfoxaflor was 6.25 parts per million (ppm) or 25 ppm. The compositions formed from base formulations A, B, C, D and E were applied to soil in the cups as a spray generated by atomization with a common agricultural pressure nozzle. A conventional aqueous sulfoxaflor suspension concentrate pesticide (aqueous sulfoxaflor SC Comparison A) and untreated check without sulfoxaflor were maintained for purposes of comparison. Microbial degradation was initiated following soil treatment by maintaining optimum soil moisture and temperature. The treatment was established and allowed microbial degradation for 11 days after treatment (DAT). Cabbage seedlings were planted into treated soils when the desired degradation period was achieved. The cabbage seedlings were allowed to establish for two days in the soil and, thereafter, were infested with green peach aphids to determine bioavailability of sulfoxaflor. The number of live aphids on each plant was determined two days after infestation. Table 4 shows the number of live aphids remaining on plants treated with compositions, including one of base formulations A, B, C, D and E two days after infestation.

TABLE 4

Number of Green Peach Aphids Remaining on Cabbage Plants

| Composition | Sulfoxaflor Concentration (ppm) | Number of Aphids Remaining[1] |
|---|---|---|
| A | 25.00 | 8 |
| | 6.25 | 14 |
| B | 25.00 | 5 |
| | 6.25 | 12 |
| C | 25.00 | 3 |
| | 6.25 | 14 |
| D | 25.00 | 7 |
| | 6.25 | 15 |
| E | 25.00 | 7 |
| | 6.25 | 13 |
| Comparison A | 25.00 | 14 |
| | 6.25 | 21 |
| untreated check | 0 | 30 |

[1]Average of four trial replicates.

Based on initial observations (Table 4), the compositions formed from the base formulations A, B, C, D and E demonstrated effectiveness in preventing bacterial degradation of sulfoxaflor compared to the aqueous sulfoxaflor SC and the untreated sample. At 25 ppm these compositions were from about 43% to about 79% better at controlling the aphids. Additionally, at 6.25 ppm these compositions were from about 29% to about 43% better at controlling the aphids.

Example 2

Preparation of Insecticidal Formulations Including β-Cyclodextrin

A sulfoxaflor solution was formed by dissolving 0.37 g sulfoxaflor in 10 g of ethanol (Solution A). A second sulfoxaflor solution was formed by dissolving 0.37 g of sulfoxaflor in 10 g of methanol (Solution B).

Two β-cyclodextrin solutions were each prepared by combining 1 g of β-cyclodextrin with 10 g deionized (DI) water and applying heat (about 70° C.) until the β-cyclodextrin was fully dissolved in the deionized water. Solution A and Solution B were individually combined with one of the β-cyclodextrin solutions to form mixtures. The mixtures were stirred under continued heat (about 70° C.) for about 30 minutes. The heat source was removed and the mixtures were stirred for about 4 hours. During cooling, the solutions turned cloudy and solid precipitates formed. The solid precipitates were individually removed from the remaining solutions by a conventional filtering process and dried.

The solids formed from the sulfoxaflor Solution A contained about 26 wt % sulfoxaflor and about 74 wt % β-cyclodextrin. The solids formed from the sulfoxaflor Solution A and β-cyclodextrin solution were determined to have a melting point of about 162° C. to about 163° C. The melting point of β-cyclodextrin is greater than 300° C.

The solids formed from the sulfoxaflor Solution B contained about 26 wt % sulfoxaflor and about 74 wt % β-cyclodextrin. The solids formed from the sulfoxaflor Solution B and β-cyclodextrin solution were determined to have a melting point of about 160° C. to about 163° C.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A pesticidal composition, comprising:

(a) a base formulation comprising a weight ratio of sulfoxaflor to at least one carrier selected from a cyclodextrin, an aniline, or a 4-aminopyridine of between about 1 to 5 and about 1 to 1; and (b) a co-formulant comprising at least one of a surfactant, a dispersant, a thickener, a pH buffer, an antifreezing agent, and a diluent.

2. A pesticidal composition, comprising:

(a) a base formulation comprising a weight ratio of sulfoxaflor to at least one of a phenol, a cyclodextrin, an aniline, and a pyridine of between about 1 to 5 and about 1 to 1; and (b) a co-formulant comprising a non-aqueous liquid diluent and a self-emulsifiable ester.

3. The pesticidal composition of claim 1, wherein the melting point of the base formulation is less than the melting point of the at least one of a cyclodextrin, an aniline, and a 4-aminopyridine.

4. The pesticidal composition of claim 1, wherein the weight ratio of the sulfoxaflor to the at least one carrier selected from a cyclodextrin, an aniline, or a 4-aminopyridine is about 1 to 2.

5. The pesticidal composition of claim 2, wherein the at least one of a phenol, a cyclodextrin, an aniline, and a pyridine comprises at least one of 4-tert-butylphenol, 2,4-di-tert-butylphenol, 4-methylphenol, 4-phenylphenol, 2-phenylphenol, 4-chlorophenol, 4-(1,1-dimethylpropyl)-phenol, 4-(1,1,2,2-tetramethylpropyl)-phenol, 4-dodecylphenol, 4-cyclohexylphenol, 4-(perchlorocyclohexyl)-phenol, 4-(4-methoxycyclohexyl)-phenol, 4-benzylphenol, 4-(1-methyl-1-phenylethyl)-phenol, 4-[1-methyl-1-(4-chlorophenyl)- ethyl]-phenol, 4-(2-chlorophenyl)-phenol, 4-(4-fluorophenyl)-phenol, 4-(4-tert-butylphenyl)-phenol, 4-(pentachlorophenyl)-phenol, 4-(4-nitrophenyl)-phenol, 4-(pentachlorophenyl)-phenol, 4-(2-pyridyl)-phenol, 4-(2-oxazolyl)-phenol, 4-(4-pyridyl)-phenol, 4-(4-morpholinyl)-phenol, 2-chloro-4-methylphenol, 3-chloro-4-tert-butyl-phenol, 2-fluoro-4-tert-butylphenol, 2-methoxy-4-tert-butylphenol, 2-phenoxy-4-tert-butylphenol, 3-(4-tert-butylphenoxy)-4-tert-butylphenol, 3-(4-fluorophenoxy)-4-tert-butylphenol, 4-methoxyphenol, 4-phenoxyphenol, 4-hydroxydiphenyl-sulphone, 4-hydroxydiphenylcarbonate, 4-fluorophenol, 2,4-difluorophenol, 2,4-dichlorophenol, 3,4-dichlorophenol, 4-bromophenol, 4-iodophenol, 4-(N-methyl-amino)-phenol, 4-(N-phenylamino)-phenol, 4-N-methyl-N-phenylaminophenol, 4-hydroxybenzophenone, 4-benzoic acid-4-hydroxyphenyl ester, N-benzoyl-4-aminophenol, N-(4-hydroxyphenyl)-ethylurethane, 3,4,5-trichlorophenol, 2,3,4-trichlorophenol, 2,3-dichloro-4-methylphenol, 4-chloro-3,5-dimethylphenol, β-cyclodextrin, α-cyclodextrin, γ-cyclodextrin, 2,4,6-tri-tert-butylaniline, and 4-aminopyridine.

6. The pesticidal composition of claim 2, wherein the phenol comprises at least one of 2,4-di-tert-butylphenol, 4-chlorophenol, and 2-phenylphenol.

7. The pesticidal composition of claim 1, wherein the cyclodextrin comprises β-cyclodextrin.

8. The pesticidal composition of claim 2, wherein the co-formulant comprises cyclohexanone and a self-emulsifiable ester.

9. The pesticidal composition of claim 6, wherein the weight ratio of the sulfoxaflor to the phenol is about 1:2.

* * * * *